(12) United States Patent
Skolnick et al.

(10) Patent No.: US 10,576,563 B2
(45) Date of Patent: Mar. 3, 2020

(54) LOAD-SHARING INSERT FOR CUTTING BLADE

(71) Applicants: Edward C. Skolnick, Wharton, NJ (US); Antoine R. Kaeslin, Norwalk, CT (US)

(72) Inventors: Edward C. Skolnick, Wharton, NJ (US); Antoine R. Kaeslin, Norwalk, CT (US)

(73) Assignee: Innovations 4 Surgery, LLC, Chapel Hill, NC (US)

( * ) Notice: Subject to any disclaimer, the term of this patent is extended or adjusted under 35 U.S.C. 154(b) by 181 days.

(21) Appl. No.: 15/887,988

(22) Filed: Feb. 3, 2018

(65) Prior Publication Data

US 2019/0240751 A1   Aug. 8, 2019

(51) Int. Cl.
| | |
|---|---|
| *B23D 61/14* | (2006.01) |
| *A61B 17/14* | (2006.01) |
| *B26D 1/00* | (2006.01) |
| *B23D 61/12* | (2006.01) |
| *B23D 61/00* | (2006.01) |

(52) U.S. Cl.
CPC ............ *B23D 61/14* (2013.01); *A61B 17/144* (2016.11); *B23D 61/123* (2013.01); *B26D 1/0006* (2013.01); *B23D 61/006* (2013.01); *B23D 61/128* (2013.01)

(58) Field of Classification Search
CPC ........ B23D 61/14; A61B 17/14; A61B 17/144
See application file for complete search history.

(56) References Cited

U.S. PATENT DOCUMENTS

| | | | |
|---|---|---|---|
| 2,315,898 | A | 4/1943 | Krilow |
| 2,338,007 | A | 12/1943 | Morris |
| 5,241,883 | A | 9/1993 | Coppier |
| 5,297,345 | A | 3/1994 | Jaakola |
| 5,802,947 | A | 9/1998 | Ward |
| 5,935,143 | A | 8/1999 | Hood |
| 6,145,426 | A | 11/2000 | Ward |
| 6,532,855 | B1 | 3/2003 | Ward |
| 2006/0016315 | A1 | 1/2006 | Zorich et al. |
| 2008/0276467 | A1 | 11/2008 | Schmidt |
| 2010/0212166 | A1 | 8/2010 | Visnack |
| 2012/0198707 | A1 | 8/2012 | Blacken |

*Primary Examiner* — Christopher J Beccia
(74) *Attorney, Agent, or Firm* — Law Office of Robert M. White, PLLC

(57) ABSTRACT

A cutting blade with multiple body inserts, each comprising a load-sharing member and a flexible perimeter joint. These inserts reduce the magnitude of frictional forces acting on the blade's body. The load-sharing member, in particular, acts as a point contact between the material being cut, such as bone, and the cutting blade. As such, the frictional forces exerted act only on the load-sharing member as opposed to the entire body. By limiting the real contact area, the magnitude of friction generated during operation is reduced. Additionally, the load-sharing members create a thermally insulating space between the body and the material being cut. The functionality of these body inserts, however, relies on the flexible perimeter joint. The flexible perimeter joint isolates the effects of frictional forces to the load-sharing member by preventing direct contact between the load-sharing member and the surrounding body.

11 Claims, 9 Drawing Sheets

LOAD-SHARING INSERT FOR CUTTING BLADE

CROSS-REFERENCES TO RELATED APPLICATION

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not Applicable.

BACKGROUND OF INVENTION

1. Field of Invention

The present invention relates to the field of cutting blades. Specifically, the present invention relates to the field of surgical blades capable of cutting biological tissues such as bone and cartilage.

2. Description of Related Art

Traditional surgical saws, such as oscillating saws and reciprocating saws, allow surgeons to cut bones (i.e. Perform osteotomies) having relatively large diameters, such as the tibia and femur. These types of surgical saws, however, which are similar in many ways to toothed saws used to cut wood, metal, and plastic, have significant disadvantages with respect to a patient's well-being. Because these surgical saws utilize rapid motion of a serrated saw blade to cut biological tissues, such as bone, a significant amount of heat is generated at the blade and bone interface due to considerable frictional forces. This can be harmful to the patient since prolonged exposure of osteocytes, or bone cells, to temperatures at or in excess of 47° C. leads to necrosis of those cells. Osteonecrosis, which is irreversible, leads to weakened bones and delayed healing. Another disadvantage of these oscillating and reciprocating bone saws is that they produce uneven cuts, preventing ideal realignment and reduction of the osteotomy gap, which is also detrimental to efficient healing of the bone. More so, these types of bone saws can tear neighboring soft tissues that are inadvertently caught in the serrations of the rapidly moving blade. Tearing of these soft tissues leads to significant blood loss and potential nerve damage.

These types of bone saws have employed a variety of measures to address these disadvantages. With respect to excessive heat generation, separate or integrated irrigation systems can be utilized to flush the osteotomy site at the interface between the cutting edge and the bone being cut (U.S. Pat. Nos. 4,008,720; 5,087,261; 5,122,142). Although effective at flushing an osteotomy site of unwanted sources of added friction (e.g. Bone particulate matter), these irrigation systems are relatively ineffective at actually cooling the entire blade. More so, irrigation negatively affects a surgeon's visualization of the osteotomy site. Just as with saws used to cut wood, metal, and plastic, rough or uneven cuts can be minimized by using a saw blade incorporating more teeth along the edge of the blade or teeth having differing angles. While this can produce a relatively finer cut, the resulting cut still leaves much to be desired in terms of producing smooth, even bone surfaces. Cutting guides, which help to stabilize the blade and keep it on a prescribed plane, are often utilized during an osteotomy to improve the precision of the cut (U.S. Pat. Nos. 5,897,559; 8,337,503). Still, the improvement is not substantial enough to consider any of these measures a long-term solution. Although efforts are taken to protect soft tissues from damage and prevent significant blood loss, the inherently close confines typical in performing any osteotomy make it extremely difficult to completely eliminate such damage, especially to tissues unseen or positioned beneath the bone being cut. This is compounded by the fact that the saw blades used with many oscillating and reciprocating bone saws are relatively large, leaving little room to maneuver.

A variety of ultrasonic surgical devices are now utilized in a number of surgical procedures, including surgical blades that are capable of cutting biological tissues such as bone and cartilage. These types of saw blades are powered by high-frequency and high-amplitude sound waves, consequent vibrational energy being concentrated at the cutting edge by way of an ultrasonic horn. Being powered by sound waves, neighboring soft tissues are not damaged by these types of blades because the cutting edge effectively rebounds from the soft tissue due to its elasticity. Thus, the significant blood loss common with use of traditional bone saws is prevented. Because the cutting edge of an ultrasonic bone cutting device is a continuous sharpened edge having no serrations, the resultant cuts are more even and there is less deflection than when using blades with serrations. As such, ultrasonic bone cutting devices facilitate more effective reduction of the osteotomy gap and enable the surgeon to better manipulate the instrument. Although ultrasonic bone cutting devices are advantageous in that they are less likely to tear neighboring soft tissues and more likely to produce relatively more even cuts, these types of blades can still generate considerable amounts of heat.

As with traditional bone saws, separate or integrated irrigation systems are often utilized in order to flush the osteotomy site and generally provide some measure of cooling effect at the cutting edge (U.S. Pat. Nos. 5,188,102; 6,379,371, 8,348,880). However, many of these blades suffer from the same disadvantages as traditional bone saws that have tried to incorporate similar measures. The excessive heat generated using any bone cutting blade is focused most significantly along the body of the blade as it translates through the bone. In particular, the normal forces generated by the bone compressing the blade body during translation coupled with the surface topography of the freshly cut bone surfaces are responsible for a majority of the friction and, therefore, heat generated during an osteotomy. While irrigant discharged at the cutting edge may have some effect in flushing debris away from the osteotomy site and providing some measure of cooling at that specific point, these irrigation systems do little to cool the entire blade body and, more importantly, the bone surfaces in direct contact with the blade body. Further, these irrigation systems can severely frustrate a surgeon's visualization of the osteotomy site.

Other types of cutting blades, such as unpowered knives used to cut vegetables and meat or circular saw blades used to cut wood, have taken a different approach to addressing some of these concerns. It is generally understood that increasing the real contact area (i.e. As opposed to the apparent contact area) between two surfaces will lead to more friction being generated when these surfaces are put in relative motion to one another. Lubrication between sliding surfaces is one way to help alleviate this problem. However, minimizing the real contact area between sliding surfaces can also be beneficial.

For example, a slicing knife disclosed in U.S. Pat. No. 5,297,245 incorporates multiple raised ridges spaced along and perpendicular to the longitudinal axis of the blade's body. These ridges are raised relative to the rest of the blade body such that the material being cut comes in contact with only those ridges during operation. In a similar fashion, a circular saw blade disclosed in U.S. Pat. No. 5,802,947 incorporates multiple dimples in the blade's body, the circumference of each dimple being raised relative to the body. A such, it is believed that the wood surfaces come in contact with only the raised circumference of the dimples during operation. US 20120198707 discloses a cutlery implement with release bumps, which serve as point contacts reducing the real contact area between the material being cut and the blade body. The knife blade disclosed in US 20100212166 also incorporates multiple protrusions similar to the "release bumps" disclosed in the previous reference. However, the bumps disclosed in US 20100212166 can be formed separately from the blade and later affixed as a "retro-fit improvement" to the blade body. These bumps may be made of metal, polymer, ceramic, or silicone, which are affixed using an adhesive. Each of these references has in common the idea that reducing the real contact area of the blade with respect to the material being cut can help reduce the magnitude of frictional forces generated during operation.

While introducing limited point contacts on a surface can help reduce the magnitude of friction generated when that surface is in contact with and in relative motion to an adjacent surface, a considerable amount of friction can still be generated. Because these limited point contacts are inseparable from the blade body, as in U.S. Pat. No. 5,297, 245, or adhered directly to the blade body, as in US 2010021266, the friction generated at these point contacts necessarily affects the blade body they are an inherent part of or directly connected to. In particular, the heat generated at these point contacts is immediately transferred to the surrounding blade body. More so, since friction is a force resisting the motion of sliding surfaces, the overall motion of the entire blade is negatively effected by this resistance. In other words, because these point contacts are inseparable from or adhered directly to the blade body, frictional forces generated at these point contacts are necessarily coupled to the entire blade.

Aside from the potential to generate significant frictional forces, normal forces can have a considerable effect on the performance of a cutting blade. In contrast to frictional forces, normal forces are exerted even when the blade is at rest. Normal forces are, in general, the compressive forces the material being cut exerts on the blade body. Because the blade body can be compressed only so much, depending on the material it is composed of, the blade body itself will exert normal forces back on to the material being cut. For example, as a circular saw blade cuts through a large cross-section of wood, such as a 2"×10", the freshly-cut wood surfaces on either side press against the blade's body. This is a primary cause of binding, where the blade seizes during operation because it cannot, in part, overcome the normal forces exerted on it. There are various approaches a woodworker can employ, such as making another pass with the blade or spreading the resulting two halves of the board slightly apart while cutting, which essentially minimize the effect of normal forces on the blade.

While surface topography plays a critical role with respect to frictional forces, substantially more friction can be generated when increasing amounts of normal forces come into play. Considering the ridges, bumps, and protrusions disclosed in the above references, these surface modifications are disclosed as being inseparable from the blade body, either as inherent features introduced during blade manufacture or statically adhered to the surface post-manufacture. In either case, these point contacts are coupled directly to the blade body and, consequently, frictional forces acting on these point contacts are necessarily coupled to the blade body and, in fact, the entire blade. As such, frictional forces negatively affect the overall efficiency of the blade and allow considerable heat transfer along the blade body.

While irrigation directed specifically toward the cutting edge may provide some measure of cooling at that particular interface, irrigation alone is inadequate for avoiding prolonged exposure of bone tissue to temperatures in excess of 47° C. Introducing surface modifications (i.e. Point contacts) during blade manufacture, such as bumps or ridges, may limit the generation of friction due to a reduction of real contact area. However, these surface modifications are coupled directly to the blade body and, consequently, couple the effects of frictional forces acting on these surface modifications to the entire blade. Therefore, there remains a need for a surgical device capable of cutting bones with large cross-sections, such as the femur, while maintaining a working temperature along the entirety of the blade body that does not impair the device's cutting efficiency, inhibit proper healing of the bone tissue or unnecessarily hinder a surgeon's visualization.

BRIEF SUMMARY OF INVENTION

According to one embodiment, an ultrasonic surgical blade capable of cutting or otherwise transforming biological tissues comprises a plurality of sockets along the blade's body and a plurality of body inserts. The body insert comprises a flexible perimeter joint and a load-sharing member. Each flexible perimeter joint encircles and is fitted to the load-sharing member. This body insert, comprising the flexible joint and load-sharing member, is then fitted into the socket. As such, the flexible perimeter joint surrounds the outer perimeter of the load-sharing member and separates the socket from the load-sharing member.

The load-sharing member has a height profile greater than the thickness (e.g. Distance between top planar surface and bottom planar surface) of the blade body. Both the top end and the bottom end of the load-sharing member are preferably convex. Further, it is preferred that the initial slope (or angle of inclination) relative to the blade body be sufficiently less than 90° in order to facilitate easy translation of each load-sharing member into the cutting plane. As the blade translates through the bone, this raised profile allows the load-sharing member to support a significant portion of the normal forces that would otherwise be exerted on the blade body alone. In addition, because the convex load-sharing members provide a limited number of point contacts, thereby limiting the real contact area of the blade that is in direct contact with adjacent bone surfaces, the frictional forces generated during translation are significantly reduced. This reduction is bolstered by the fact that each load-sharing member is preferably composed of material having a low coefficient of friction.

The flexible perimeter joint, which effectively prevents direct contact between the surrounding blade body and the load-sharing member, serves critical decoupling and dampening roles. In particular, the flexible perimeter joint imparts at least three degrees of freedom (DOF) to the load-sharing member, thereby isolating the effects of frictional forces exerted on the load-sharing member. It is preferred that the width of the flexible perimeter joint (i.e. Distance between the inner edge and the outer edge) be at least equal to the stroke length of the cutting blade, which may vary depending on whether the cutting blade is powered by ultrasonic vibrations, oscillating motion, or reciprocating motion. Other factors can have an effect on the width of the flexible perimeter joint, as well. As such, those forces are decoupled from the blade body, thereby improving the cutting efficiency of the blade and limiting the production of heat along the blade body. In addition, the flexible perimeter joint can act as a dampening barrier, inhibiting the transfer of vibrations from the blade body to the load-sharing member, thereby inhibiting the generation of additional frictional forces that would otherwise be exerted at the interface between the load-sharing member and bone surface.

While the load-sharing member, working in conjunction with the flexible perimeter joint, functions to limit frictional forces from acting on the blade body, this member also provides an insulative barrier and space for the translation of surgical debris (e.g. Bone particulate matter). In particular, the raised profile of the load-sharing member creates an air-filled space between the bone surfaces and the blade body. Air, having a thermal conductivity (k) of 0.024 W/mK at 25° C., is a much better alternative to an irrigant, for example, which is composed primarily of a saline solution having a thermal conductivity of 0.6 W/mK at 25° C. As an insulative barrier, this space reduces the conduction of heat generated along the blade body to the adjacent bone surfaces. Further, this space allows relatively free movement of surgical debris, thereby preventing additional friction that would otherwise be generated if the surgical debris is effectively trapped between the blade body and the bone surface.

Figure 1:
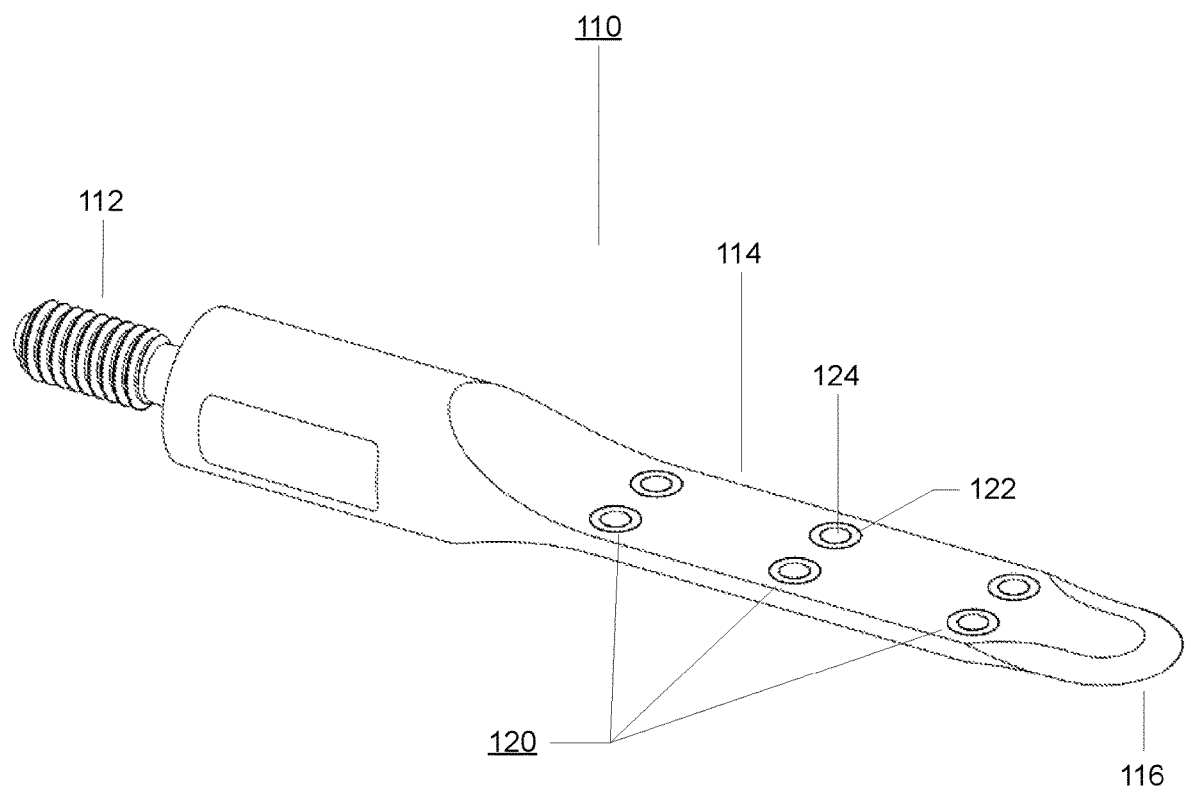
FIG. 1 is a perspective view illustrating one embodiment of an ultrasonic blade attachment.

REFERENCE NUMERALS FOR DRAWINGS
(PLEASE NOTE THAT FIRST DIGIT INDICATES THE FIGURE IN WHICH A COMPONENT IS FIRST VISUALLY-IDENTIFIABLE)

110 Ultrasonic blade attachment
112 Attachment end
114 Blade body
116 Cutting end
120 Body insert
122 Flexible perimeter joint
124 Load-sharing member
314 Blade body
316 Cutting end
318 Socket
320 Body insert
322 Flexible perimeter joint
324 Load-sharing member
410 Ultrasonic blade attachment
412 Attachment end
414 Blade body
416 Cutting end
420 Body insert
422 Flexible perimeter joint
424 Load-sharing member
426 Debris relief cut-out
514 Blade body
516 Cutting end
518 Socket
520 Body insert
522 Flexible perimeter joint
524 Load-sharing member
610 Oscillating blade attachment
612 Attachment end
614 Blade body
616 Cutting end
620 Body insert
622 Flexible perimeter joint
624 Load-sharing member
718 Socket
810 Oscillating blade attachment
812 Attachment end
814 Blade body
816 Cutting end
820 Body insert
822 Flexible perimeter joint
824 Load-sharing member
826 Debris relief cut-out
910 Reciprocating blade attachment
912 Attachment end
914 Blade body
916 Cutting end
920 Body insert
922 Flexible perimeter joint
924 Load-sharing member

DETAILED DESCRIPTION OF DRAWINGS

FIG. 1 is a perspective view of one embodiment of an ultrasonic blade attachment 110. The ultrasonic blade attachment 110 comprises an attachment end 112, a blade body 114, and a cutting end 116. The blade body 114, in particular, comprises a plurality of sockets 318 and a plurality of body inserts 120. An embodiment of the socket 318 is better visualized in FIG. 3. The body insert 120 comprises a flexible perimeter joint 122 and a load-sharing member 124. The flexible perimeter joint 122 encircles and is fitted to the load-sharing member 124. The flexible perimeter joint 122 is fitted into the socket 318. As such, the flexible perimeter joint 122 separates the load-sharing member 124 from the surrounding blade body 114.

The load-sharing member 124 has a height profile greater than the thickness of the blade body 114, such that the load-sharing member 124 extends perpendicularly some measure from both the top planar surface and bottom planar surface of the blade body 114. It is preferred that both the top end and the bottom end of the load-sharing member be convex. It is preferred that the load-sharing member 124 extend in either direction a distance minimally sufficient to allow free movement of bone particulate matter along the blade body 114 as the blade translates, for example, through the bone being cut. It is believed that freely moving bone particulate matter can alleviate a significant amount of frictional forces that would otherwise be generated between the bone surfaces and the blade body 114. It is preferred that the load-sharing member 124 be composed of a material having a low coefficient of friction and low thermal conductivity, including but not limited to ceramics (e.g. Alumina), polymers (e.g. Teflon, Victrex, PEEK) and other materials satisfying this criteria.

Typically, a bone saw blade with no improvements is acted upon, during translation through the bone, by significant frictional forces. These forces affect not only the efficiency of the blade but lead to the generation of excessive heat at the interface between bone and blade. In general, the magnitude of frictional forces generated at this interface depends on the friction coefficient of the materials in direct contact with one another and the normal forces exerted on each surface. The normal forces are the compressive forces of the bone, above and below, acting on the blade. These normal forces act on the blade even when the blade is not translating through the bone or, in other words, is at rest. Once the blade is in motion relative to the bone surfaces, the surface topography, physical properties, and chemical properties of each surface (e.g. Blade and bone) in conjunction with the normal forces are responsible, in large part, for the magnitude of frictional forces generated during translation.

The load-sharing member 124, having a raised profile relative to the thickness of the blade body 114, allows each load-sharing member 124 to act as a point contact with adjacent bone surfaces. As such, normal forces act directly on these point contacts or load-sharing members 124. Further, introducing a limited number of point contacts along the blade body 114 effectively reduces the real contact area of the blade body 114, which necessarily decreases the magnitude of frictional forces normally generated between the blade body 114 and adjacent bone surfaces. Lastly, the raised profile of the load-sharing members 124 creates a space between the blade body 114 and the adjacent bone surfaces. This space not only provides a thermally insulating barrier between the blade body 114 and adjacent bone surfaces but also allows bone particulate matter, resulting from the cutting action, to move relatively freely along the blade body 114.

The flexible perimeter joint 122, however, is integral to the proper functioning of this body insert 120. While the load-sharing member 124, as a point contact, is acted upon by frictional forces, these forces must be decoupled from the surrounding blade body 114. In other words, these forces must not adversely affect the efficiency of the ultrasonic bone cutting device or lead to the generation of excessive heat along the blade body 114. With this in mind, the flexible perimeter joint 122 prevents direct contact between the load-sharing member 124 and the surrounding blade body 114. It is preferred that the flexible perimeter joint 122 be composed of an elastomer, such as silicone. In addition, it is preferred that the material have low thermal conductivity.

While also imparting at least three degrees of freedom to the load-sharing member 124, the elastic properties of the flexible perimeter joint 122 isolate frictional forces so that they act on the load-sharing member 124 alone. The elastic properties of the flexible perimeter joint 122 also provide a means of buffering the load-sharing member 124 from the vibrations that propagate along the blade body 114. Because an ultrasonic device utilizes high-frequency, high-amplitude sound waves to rapidly vibrate an end effector, such as the cutting end 116 of the ultrasonic blade attachment 110, vibrations along the blade body 114 can substantially increase the magnitude of frictional forces generated at the bone surface and blade body 114 interface. Therefore, it is important to limit the effect vibrations may have on the load-sharing member 124 since the load-sharing member 124 is in direct contact with adjacent bone surfaces, where it is already acted upon by considerable frictional forces.

Figure 2:
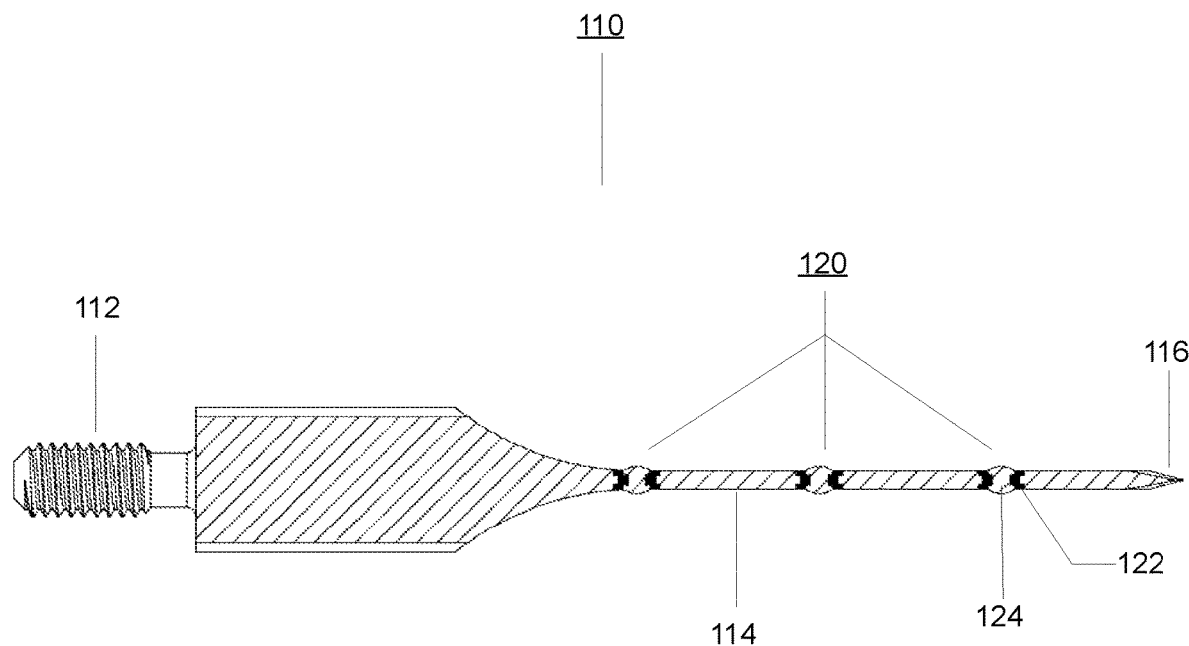
FIG. 2 is a cross-sectional side profile view of one embodiment of an ultrasonic blade attachment.

FIG. 2 is a cross-sectional side profile view of one embodiment of an ultrasonic blade attachment 110 comprising an attachment end 112, a blade body 114, and a cutting end 116. The blade body 114, in particular, comprises a plurality of sockets 318 and a plurality of body inserts 120. An embodiment of the socket 318 is better visualized in FIG. 3. Each body insert 120 comprises a flexible perimeter joint 122 and a load-sharing member 124. FIG. 2 illustrates the raised profile of the load-sharing member 124 relative to the top and bottom planar surfaces of the blade body 114. In addition, FIG. 2 demonstrates one manner of fitting the load-sharing member 124 to the flexible perimeter joint 122 and fitting the flexible perimeter joint 122 within the socket 318 of the blade body 114. It is also apparent from FIG. 2 that the flexible perimeter joint 122 separates the load-sharing member 124 from the surrounding blade body 114.

Figure 3:
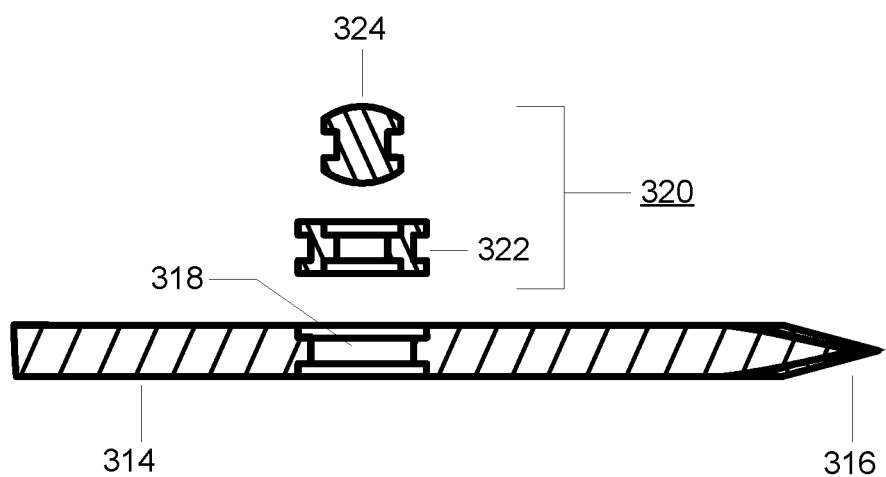
FIG. 3 is a close-up, cross-sectional, and exploded side view of one embodiment of a blade insert and socket.

FIG. 3 is a close-up, cross-sectional and exploded side view of one embodiment of a body insert 320 and a socket 318. A blade body 314 and a cutting end 316 are also visible in FIG. 3. Each body insert 320 comprises a flexible perimeter joint 322 and a load-sharing member 324. FIG. 3 best illustrates the socket 318 within which the body insert 320, in general, and flexible perimeter joint 322, in particular, is fitted. FIG. 3 also demonstrates one manner in which the load-sharing member 324 is encircled by and fitted to the flexible perimeter joint 322. It should be noted that fitting the flexible perimeter joint 322 to the load-sharing member 324 and fitting the flexible perimeter joint 322 within the socket 318 can be accomplished using any variety of press-fit, slip-fit, snap-fit, adhesive, any combination thereof, or other suitable means.

Figure 4:
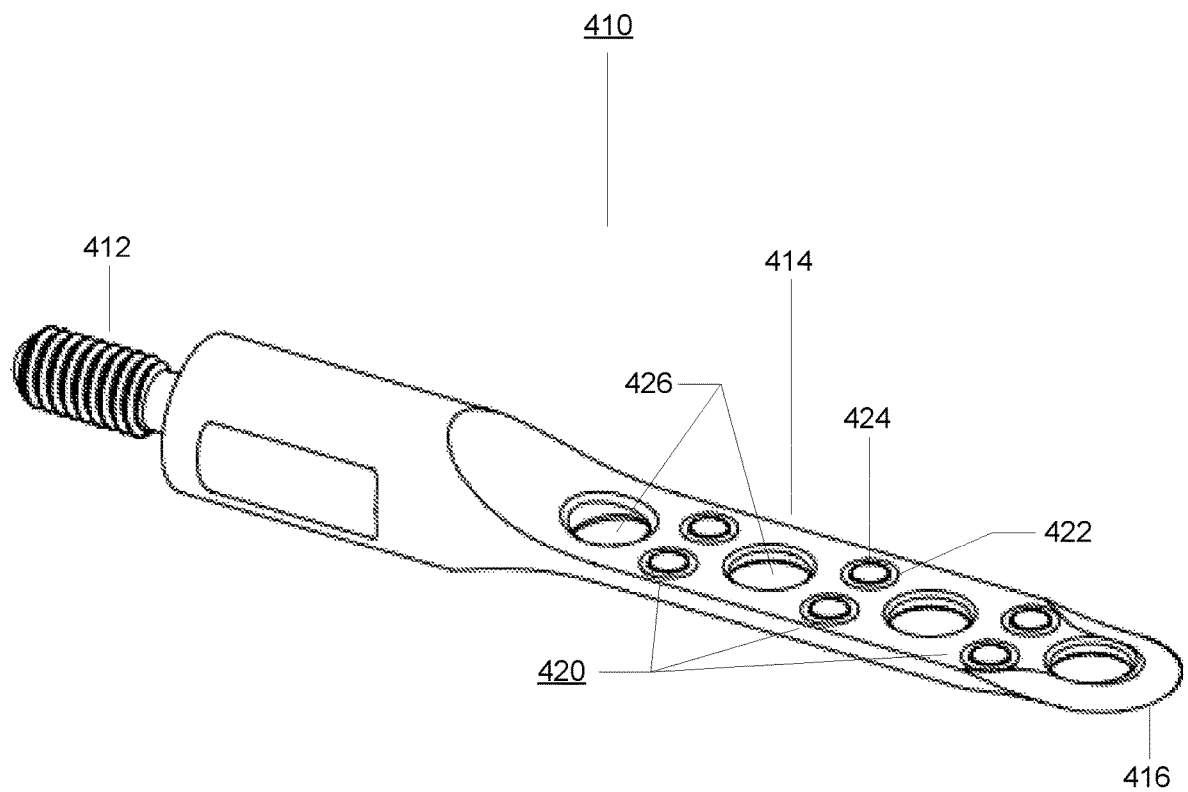
FIG. 4 is a perspective view of another embodiment of an ultrasonic blade attachment.

FIG. 4 is a perspective view of another embodiment of an ultrasonic blade attachment 410 comprising an attachment end 412, a blade body 414, and a cutting end 416. The blade body 414, in particular, comprises a plurality of sockets 318, a plurality of body inserts 420, and at least one debris relief cut-out 426. An embodiment of the socket 318 is better visualized in FIG. 3. Each body insert 420 comprises a flexible perimeter joint 422 and a load-sharing member 424. The debris relief cut-out 426 is an opening in the blade body 414 that extends from the top planar surface to the bottom planar surface of the blade body 414. As bone particulate matter moves freely along the blade body 414, the debris relief cut-out 426 can capture the bone particulate matter, thereby preventing excessive build-up of bone particulate matter along the blade body 414 and otherwise further limiting its potential to generate additional frictional forces.

Figure 5:
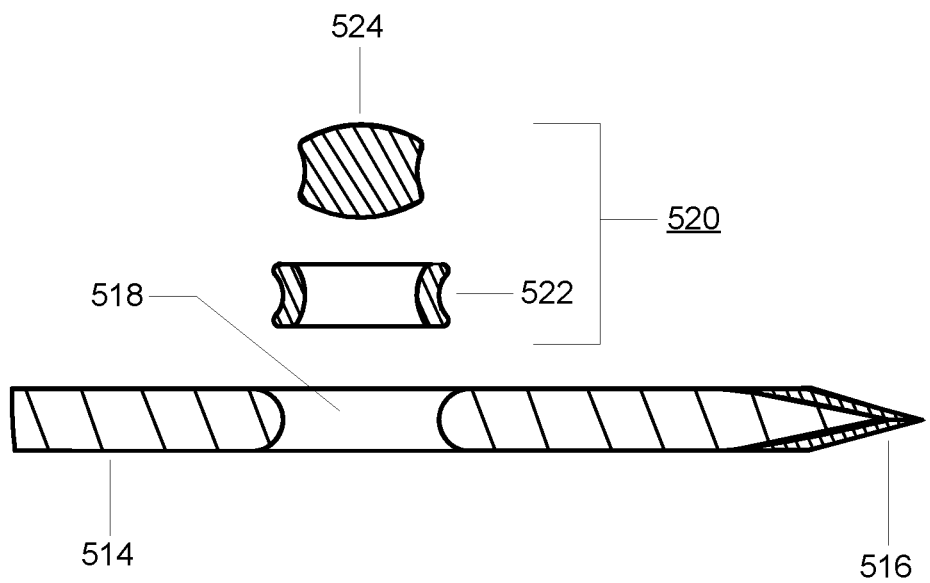
FIG. 5 a close-up, cross-sectional, and exploded side view of another embodiment of a blade insert and socket.

FIG. 5 is a close-up, cross-sectional and exploded side view of another embodiment of a body insert 520 and a socket 518. A blade body 514 and a cutting end 516 are also visible in FIG. 5. Each body insert 520 comprises a flexible perimeter joint 522 and a load-sharing member 524. FIG. 5 best illustrates the socket 518 within which the body insert 520, in general, and flexible perimeter joint 522, in particular, is fitted. FIG. 5 also demonstrates one manner in which the load-sharing member 524 is encircled by and fitted to the flexible perimeter joint 522. It should be noted that fitting the flexible perimeter joint 522 to the load-sharing member 524 and fitting the flexible perimeter joint 522 within the socket 518 can be accomplished using any variety of press-fit, slip-fit, snap-fit, adhesive, any combination thereof, or other suitable means.

Figure 6:
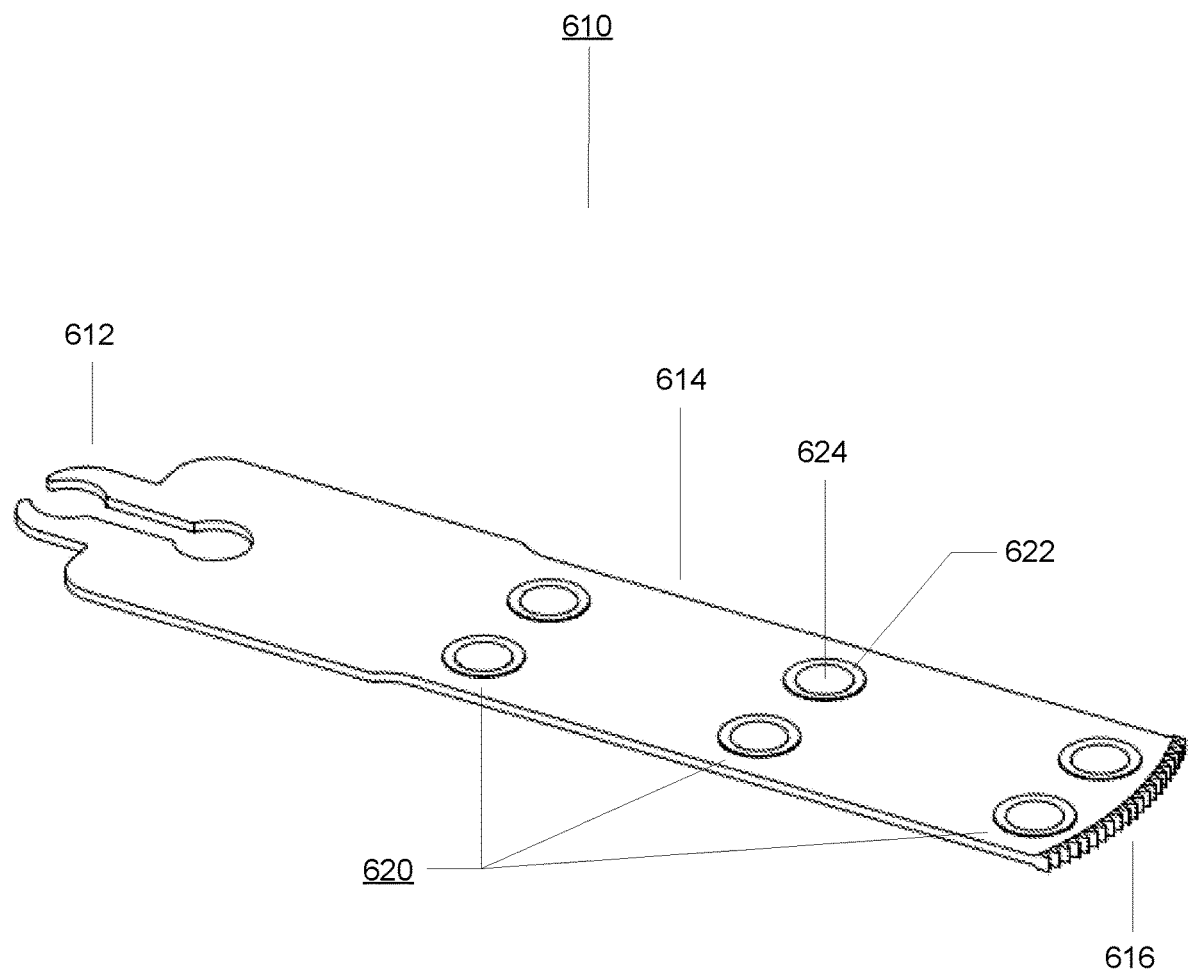
FIG. 6 is a perspective view of one embodiment of an oscillating blade attachment.

FIG. 6 is a perspective view of one embodiment of an oscillating blade attachment 610. The oscillating blade attachment 610 comprises an attachment end 612, a blade body 614, and a cutting end 616. The blade body 614, in particular, comprises a plurality of sockets 718 and a plurality of body inserts 620. An embodiment of the socket 718 is better visualized in FIG. 7. The body insert 620 comprises a flexible perimeter joint 622 and a load-sharing member 624. The flexible perimeter joint 622 encircles and is fitted to the load-sharing member 624. The flexible perimeter joint 622 is fitted into the socket 718. As such, the flexible perimeter joint 622 separates the load-sharing member 624 from the surrounding blade body 614.

Figure 7:
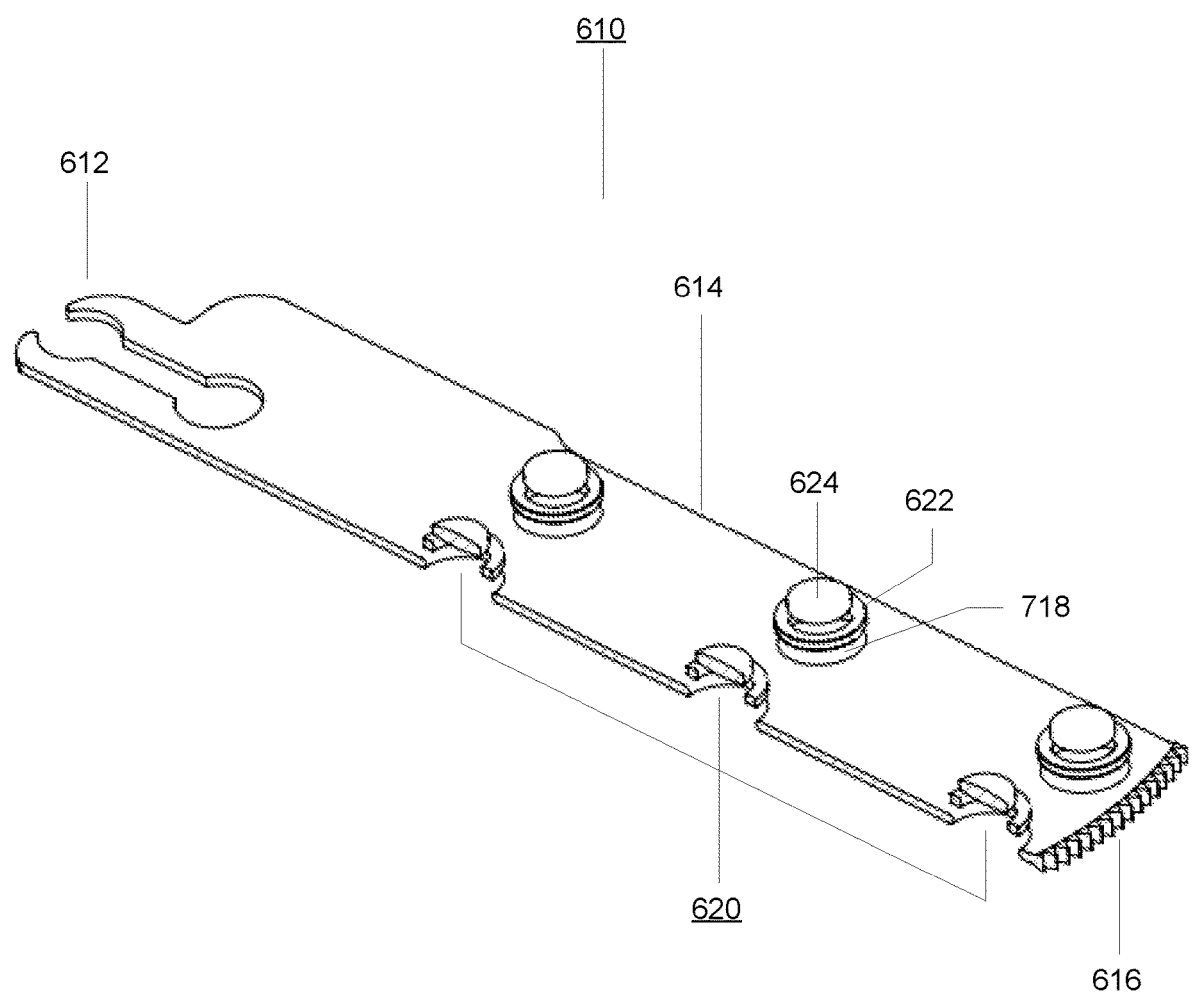
FIG. 7 is a cross-sectional perspective view of one embodiment of an oscillating blade attachment.

FIG. 7 is a cross sectional perspective view of one embodiment of an oscillating blade attachment 610. The oscillating blade attachment 610 comprises an attachment end 612, a blade body 614, and a cutting end 616. The blade body 614, in particular, comprises a plurality of sockets 718 and a plurality of body inserts 620. The body insert 620 comprises a flexible perimeter joint 622 and a load-sharing member 624. The flexible perimeter joint 622 encircles and is fitted to the load-sharing member 624. The flexible perimeter joint 622 is fitted into the socket 718. As such, the flexible perimeter joint 622 separates the load-sharing member 624 from the surrounding blade body 614.

Figure 8:
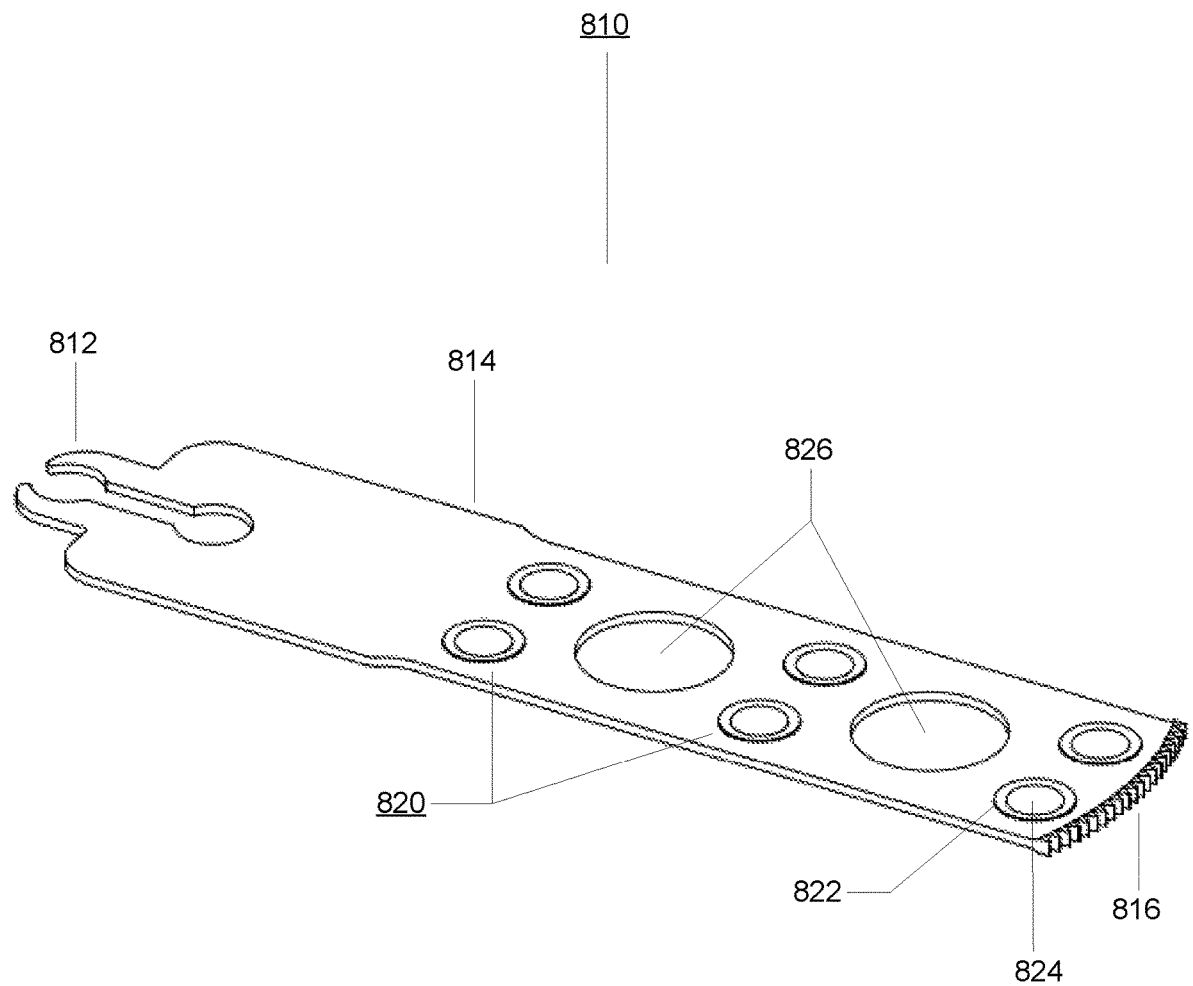
FIG. 8 is a perspective view of another embodiment of an oscillating blade attachment.

FIG. 8 is a perspective view of another embodiment of an oscillating blade attachment 810 comprising an attachment end 812, a blade body 814, and a cutting end 816. The blade body 814, in particular, comprises a plurality of sockets 718, a plurality of body inserts 820, and at least one debris relief cut-out 826. An embodiment of the socket 718 is better visualized in FIG. 7. Each body insert 820 further comprises a flexible perimeter joint 822 and a load-sharing member 824. The debris relief cut-out 826 is an opening in the blade body 814 that extends from the top planar surface to the bottom planar surface of the blade body 814. As bone particulate matter moves freely along the blade body 814, the debris relief cut-out 826 can capture the bone particulate matter, thereby preventing excessive build-up of bone particulate matter along the blade body 814 and otherwise further limiting its potential to generate additional frictional forces.

Figure 9:
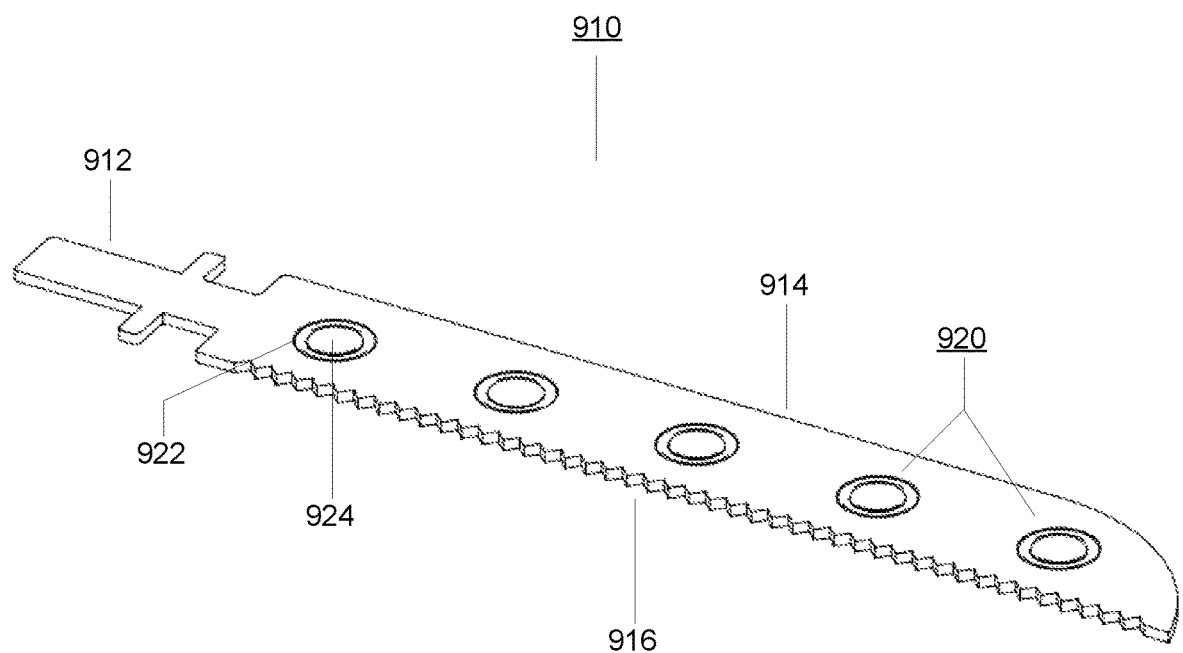
FIG. 9 is a perspective view of one embodiment of a reciprocating blade attachment.

FIG. 9 is a perspective view of one embodiment of a reciprocating blade attachment 910. The reciprocating blade attachment 910 comprises an attachment end 912, a blade body 914, and a cutting edge 916. The blade body 914, in particular, comprises a plurality of sockets 718 and a plurality of body inserts 920. An embodiment of the socket 718 is better visualized in FIG. 7. The body insert 920 comprises a flexible perimeter joint 922 and a load-sharing member 924. The flexible perimeter joint 922 encircles and is fitted to the load-sharing member 924. The flexible perimeter joint 922 is fitted into the socket 718. As such, the flexible perimeter joint 922 separates the load-sharing member 924 from the surrounding blade body 914.

While specific embodiments of the present invention and applications of the invention have been described herein, it will be apparent to those of ordinary skill in the art that many variations on the embodiments and applications described herein are possible without departing from the scope of the invention described and claimed herein. It should be understood that while certain embodiments of the invention have been shown and described, the invention is not to be limited to the specific embodiments described and illustrated.

What is claimed is:

1. A bone cutting blade, comprising:
    an attachment end;
    a blade body characterized, in part, by a top planar surface, a bottom planar surface, and a blade thickness, said blade thickness being equal to a distance between said top planar surface and said bottom planar surface, said blade body comprising at least one socket, said socket extending said thickness of said blade body;
    at least one body insert comprising a flexible perimeter joint and a load-sharing member;
    said load-sharing member characterized, in part, by a margin along a transverse plane of said load-sharing member, a member height, a top end, and a bottom end, said member height being greater than said blade thickness;
    said flexible perimeter joint characterized, in part, by an inner edge and an outer edge, said inner edge being fitted to said margin of said load-sharing member, said outer edge being fitted to said socket of said blade body; and
    a cutting end;
    whereby the body insert, comprising the flexible perimeter joint fitted to the load-sharing member having a height profile greater than the blade thickness, is inserted into the socket of the blade body, such that the top end of the load-sharing member extends a measure perpendicular to the top planar surface and the bottom end of the load-sharing member extends a measure perpendicular to the bottom planar surface of the blade body, and the flexible perimeter joint separates the load-sharing member from the socket.

2. The bone cutting blade of claim 1, wherein said flexible perimeter joint is characterized, in part, by a joint width equal to a distance between said inner edge and said outer edge, said joint width being equal to or greater than a stroke length of said bone cutting blade.

3. The bone cutting blade of claim 1, wherein said load-sharing member is formed from a material having a low coefficient of friction.

4. The bone cutting blade of claim 1, wherein at least one of said flexible perimeter joint and said load-sharing member is formed from a material having a low thermal conductivity.

5. The bone cutting blade of claim 1, wherein said top end and said bottom end of said load-sharing member are convex.

6. The bone cutting blade of claim 1, wherein said blade body further comprises at least one debris relief cut-out, said debris relief cut-out extending said body thickness.

7. A bone cutting blade, comprising:
    an attachment end;
    a blade body characterized, in part, by a top planar surface, a bottom planar surface, and a blade thickness, said blade thickness being equal to a distance between said top planar surface and said bottom planar surface, said blade body comprising at least one socket, said socket extending said thickness of said blade body;
    at least one body insert comprising a load-sharing member;
    said load-sharing member characterized, in part, by a margin along a transverse plane of said load-sharing member, a member height, a top end, and a bottom end, said member height being greater than said blade thickness, said margin of said load-sharing member being fitted to said socket of said blade body; and a cutting end;

whereby the body insert, comprising the load-sharing member having a height profile greater than the blade thickness, is inserted into the socket of the blade body, such that the top end of the load-sharing member extends a measure perpendicular to the top planar surface and the bottom end of the load-sharing member extends a measure perpendicular to the bottom planar surface of the blade body.

8. The bone cutting blade of claim 7, wherein said load-sharing member is formed from a material having a low coefficient of friction.

9. The bone cutting blade of claim 7, wherein said load-sharing member is formed from a material having a low thermal conductivity.

10. The bone cutting blade of claim 7, wherein said top end and said bottom end of said load-sharing member are convex.

11. The bone cutting blade of claim 7, wherein said blade body further comprises at least one debris relief cut-out, said debris relief cut-out extending said body thickness.

\* \* \* \* \*